United States Patent
Brentano et al.

(10) Patent No.: US 10,752,944 B2
(45) Date of Patent: Aug. 25, 2020

(54) CIRCULARIZED TEMPLATES FOR SEQUENCING

(75) Inventors: Steven T. Brentano, Santee, CA (US); Dmitry Lyakhov, San Diego, CA (US); Matthew C. Friedenberg, San Diego, CA (US); Anne-Laure Shapiro, La Jolla, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 1490 days.

(21) Appl. No.: 14/342,725

(22) PCT Filed: Sep. 6, 2012

(86) PCT No.: PCT/US2012/054000
§ 371 (c)(1),
(2), (4) Date: Jun. 18, 2014

(87) PCT Pub. No.: WO2013/036668
PCT Pub. Date: Mar. 14, 2013

(65) Prior Publication Data
US 2014/0378318 A1 Dec. 25, 2014

Related U.S. Application Data

(60) Provisional application No. 61/531,580, filed on Sep. 6, 2011.

(51) Int. Cl.
*C12Q 1/68* (2018.01)
*C12Q 1/6869* (2018.01)
*C12Q 1/6855* (2018.01)
*C12Q 1/6844* (2018.01)

(52) U.S. Cl.
CPC ......... *C12Q 1/6869* (2013.01); *C12Q 1/6844* (2013.01); *C12Q 1/6855* (2013.01)

(58) Field of Classification Search
CPC ............ C12Q 1/6855; C12Q 2521/325; C12Q 2521/501; C12Q 2525/161; C12Q 2525/307
See application file for complete search history.

(56) References Cited

U.S. PATENT DOCUMENTS

| | | | |
|---|---|---|---|
| 6,235,502 B1 | 5/2001 | Weissman et al. | |
| 6,828,098 B2 | 12/2004 | Langmore et al. | |
| 7,575,860 B2 | 8/2009 | Evans et al. | |
| 8,501,405 B2 | 8/2013 | Korlach et al. | |
| 9,404,147 B2 | 8/2016 | Nelson et al. | |
| 10,184,147 B2 | 1/2019 | Nelson et al. | |
| 2003/0232348 A1 | 12/2003 | Jones et al. | |
| 2004/0216770 A1 | 11/2004 | Chen et al. | |
| 2005/0069939 A1 | 3/2005 | Wang et al. | |
| 2008/0242560 A1 | 10/2008 | Gunderson et al. | |
| 2008/0293589 A1 | 11/2008 | Shapero | |
| 2009/0181861 A1 | 7/2009 | Li et al. | |
| 2009/0280538 A1* | 11/2009 | Patel | C12N 15/10 435/91.2 |
| 2009/0298075 A1 | 12/2009 | Travers | |
| 2011/0195406 A1* | 8/2011 | Sorenson | C12N 9/1252 435/6.1 |
| 2014/0329282 A1 | 11/2014 | Nelson et al. | |
| 2019/0185917 A1 | 6/2019 | Nelson et al. | |

FOREIGN PATENT DOCUMENTS

| | | |
|---|---|---|
| EP | 1741787 A1 | 1/2007 |
| WO | WO 93/017127 A1 | 9/1993 |
| WO | WO 02/103054 A1 | 12/2002 |
| WO | WO 05/056750 A2 | 6/2005 |
| WO | 20090120372 A2 | 10/2009 |
| WO | 20100003153 A2 | 1/2010 |
| WO | WO 10/086622 A1 | 8/2010 |
| WO | WO 11/019964 A1 | 2/2011 |
| WO | WO 11/019964 A9 | 2/2011 |
| WO | WO 2011/091393 A1 | 7/2011 |

(Continued)

OTHER PUBLICATIONS

APO Patent Examination Report, Australian Patent Application No. 2012304520, dated Dec. 12, 2014.
EPO Communication Pursuant to Article 94(3) EPC, European Patent Application No. 12772164.5, dated Dec. 15, 2015.
PCT Search Report, International Application No. PCT/US2012/054000, dated Feb. 22, 2013.
PCT Preliminary Report, International Application No. PCT/US2012/054000, dated Mar. 20, 2014.
PCT Written Opinion, International Application No. PCT/US2012/054000, dated Feb. 22, 2013.
EP Application No. 19187592.1 Extended European Search Report dated Feb. 5, 2020.

(Continued)

*Primary Examiner* — David C Thomas
(74) *Attorney, Agent, or Firm* — Jeff Landes; Alston & Bird LLP

(57) ABSTRACT

The invention provides methods of forming a circular template for sequencing a target nucleic acid. The circular template is generated by amplification of a segment of the target nucleic acid with chimeric primers with complementary 5' ends. The circular template has a single nick or gap providing a site for initiation of template-directed extension for sequence analysis. Sequencing of a single template generates reads of alternating segments of the same strand of the target nucleic spaced by primer segments. The different reads of the same strand of the target nucleic acid can be compiled to generate a consensus sequence. Because only one strand of the target nucleic acid is sequenced per reaction, the present method avoids errors introduced by unwittingly combining sequences of both strands of a heteroduplex PCR product. Because only one strand of the target nucleic acid is sequenced per reaction, the present method avoids errors introduced by unwittingly combining sequences of both strands of a heteroduplex PCR product.

20 Claims, 8 Drawing Sheets

Specification includes a Sequence Listing.

(56) References Cited

FOREIGN PATENT DOCUMENTS

WO    WO 13/036668 A1    3/2013
WO    WO 13/036685 A1    3/2013

OTHER PUBLICATIONS

AU Application No. 2012304537 Notice of Acceptanc dated Aug. 6, 2015.
AU Application No. 2015246165 Examination Report No. 1 dated Dec. 2, 2016.
AU Application No. 2015246165 Examination Report No. 2 dated Jun. 16, 2017.
AU Application No. 2015246165 Notice of Acceptance dated Jul. 7, 2017.
Australian Application No. 2013304537, Patent Examination Report dated Jan. 9, 2015.
Chen et al., "Recognition of an expanded genetic alphabet by type-II restriction endonucleases and their application to analyze polymerase fidelity," Nucleic Acids Research, 39(9):3949-3961, (2011).
Drmanac et al., "Human Genome Sequencing Using Unchained Base Reads on Self-Assembling DNA Nanoarrays," Science, 1(327):78-81 (2010).
Drmanac et al., "Supporting Online Material for Human Genome Sequencing Using Unchained Base Reads on Self-Assembling DNA Nanoarrays," Science, 1(327): 78-81, (2010).
EPO Application No. 17160148.7 (Publihed as EP3225698), European Search Report and Opinion dated Aug. 28, 2017.
Ho et al., "Structure and Mechanism of RNA Ligase," Structure, vol. 12, pp. 327-339, (2004).
Silber et al., "Purification and Properties of Bacteriophage T4-Induced RNA Ligase," Proc. Nat. Acad. Sci., 69(10): 3009-3013, (1972).
Travers et al., "A flexible and efficient template format for circular consensus sequencing and SNP detection," Nucleic Acids Research, 38(15), (2010).
U.S. Appl. No. 13/720,108, Notice of Allowance dated Feb. 6, 2015.
U.S. Appl. No. 13/720,108, Notice of Allowance dated Feb. 26, 2016.
U.S. Appl. No. 13/720,108, Requirement for Restriction/Election dated Aug. 21, 2014.
U.S. Appl. No. 14/342,764, Final Office Action dated Apr. 27, 2017.
U.S. Appl. No. 14/342,764, Non-Final Office Action dated Oct. 20, 2016.
U.S. Appl. No. 14/342,764, Notice of Allowance dated Oct. 11, 2019.
U.S. Appl. No. 15/191,231, Non-Final Office Action dated Jan. 16, 2018.
U.S. Appl. No. 15/191,231, Notice of Allowance dated Sep. 18, 2018.
U.S. Appl. No. 15/191,231, Requirement for Restriction/Election dated Sep. 27, 2017.
WIPO Application No. PCT/US2012/054023, PCT International Preliminary Report on Patentability, dated Mar. 20, 2014.
WIPO Application No. PCT/US2012/054023, PCT International Search Report and Written Opinion of the International Searching Authority, dated Jan. 10, 2013.

* cited by examiner

A.  Pacific Bioscience SMRTbell design

B.  Circularized template design

SEQUENCE LISTING

<160> NUMBER OF SEQ ID NOS: 3

<210> SEQ ID NO 1
<211> LENGTH: 40
<212> TYPE: DNA
<213> ORGANISM: Artificial Sequence
<220> FEATURE:
<223> OTHER INFORMATION: Primer

<400> SEQUENCE: 1
gcccgcggaa aaaacaagtc acaaagggaa gggcaggaac                                    40

<210> SEQ ID NO 2
<211> LENGTH: 37
<212> TYPE: DNA
<213> ORGANISM: Artificial Sequence
<220> FEATURE:
<223> OTHER INFORMATION: Primer

<400> SEQUENCE: 2
ccgcgggcaa aaaggatac tcacgacgcg gacccag                                        37

<210> SEQ ID NO 3
<211> LENGTH: 44
<212> TYPE: DNA
<213> ORGANISM: Artificial Sequence
<220> FEATURE:
<223> OTHER INFORMATION: Primer

<400> SEQUENCE: 3
gcccgcggcg gcaaaaaaca agtcacaaag ggaagggcag gaac                               44

CIRCULARIZED TEMPLATES FOR SEQUENCING

CROSS-REFERENCE TO RELATED APPLICATIONS

The present application is a U.S. national stage of PCT/US2012/054000 filed Sep. 6, 2012, which claims the benefit of 61/531,580 filed Sep. 6, 2011, incorporated by reference in its entirety for all purposes

REFERENCE TO A "SEQUENCE LISTING"

The sequence listing in file 423638SEQLIST.TXT was created Dec. 14, 2012 and is 880 bytes. This sequence listing is hereby incorporated by reference.

BACKGROUND OF THE INVENTION

Some so-called next generation sequencing methods, particularly single-molecule methods, sequence a target nucleic acid from a circular template. Template-directed incorporation of nucleotides by the circular template proceeds in circles generating multiple sequencing reads of the target nucleic acid. The multiple reads may contain different sequencing errors. Combination of multiple raw sequencing reads of the target nucleic acid generates a consensus sequence reducing the errors present in individual reads.

One type of circular template is formed by ligating hairpin loop adapters to the ends of a double-stranded target nucleic acid as in the Pacific Biosciences SMRTbell™ template. The single-stranded loop portions provide primer binding sites for extension through the target nucleic acid. A sequencing read generates alternating reads of hairpin loop segments and target nucleic acid encoded by the circular template. The reads of the target nucleic acid alternate between the sense and anti-sense strands.

BRIEF DESCRIPTION OF THE FIGURES

FIG. 1 shows amplification of a target nucleic acid with a primer pair;

FIG. 2 shows digestion of the 3' ends of the amplification product with a polymerase with a 3' to 5' exonuclease activity; and FIG. 3 shows ligation of one nick in a circularized template leaving a single nick remaining.

FIG. 4 shows amplification using a primer pair in which 5' segments of the primers are of unequal length.

FIG. 5 shows exonuclease digestion of the 3' ends. FIG. 6 shows ligation of a nick, leaving an unclosed gap adjacent to a free 3' hydroxyl.

SUMMARY OF THE CLAIMED INVENTION

Figure 1:
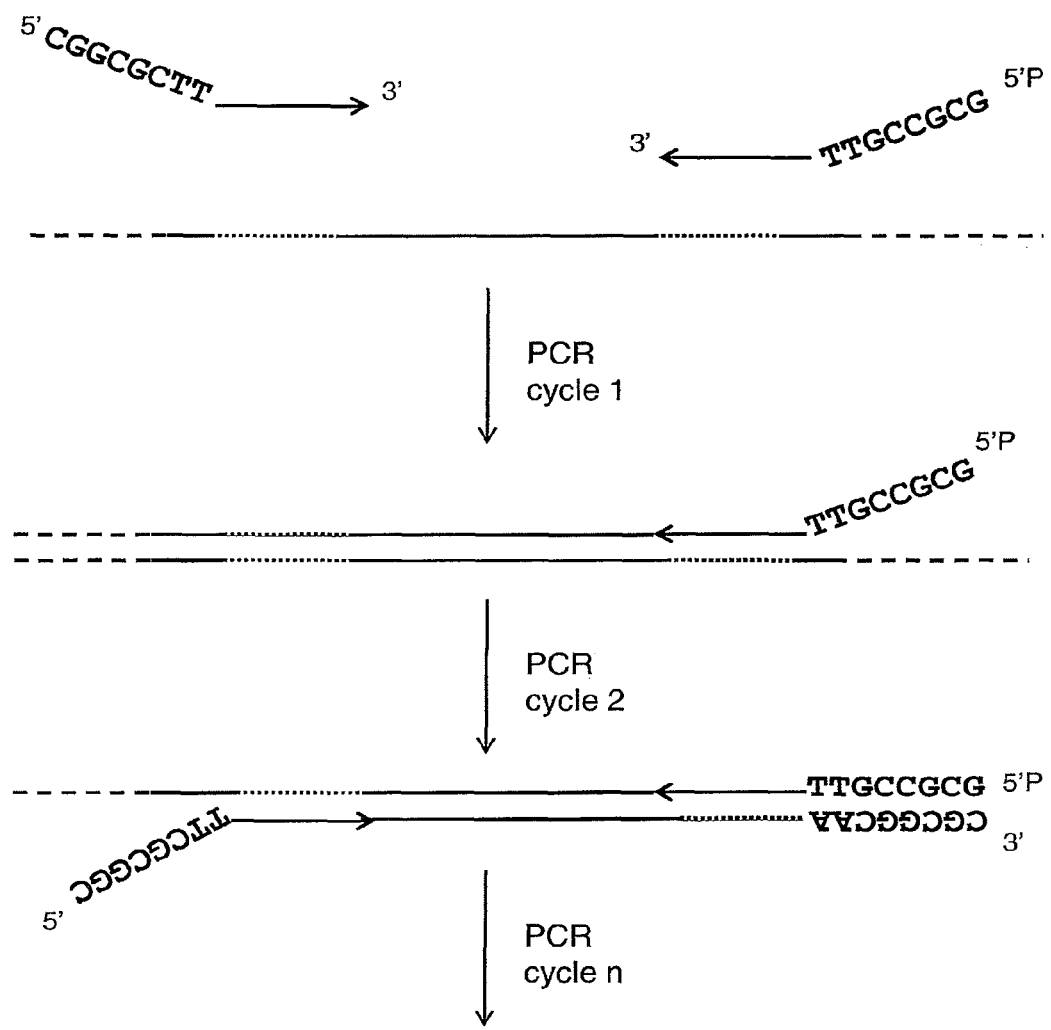
FIGS. 1-3 show a scheme for generating a circularized template with a single nick.

The invention provides methods of forming a circular template for sequencing a target nucleic acid. These methods involve contacting a target nucleic acid with a primer pair under PCR conditions. Each of the primers having a 3' segment and a 5' segment, the 3' segments of the primers being target-binding segments, the 5' segments being mutually complementary in opposing orientations, a first of the primers having a 5' phosphate group and the second of the primers lacking a 5' phosphate and/or having a shorter 5' segment than the first primer; thereby forming an amplified nucleic acid comprising a segment of the target nucleic acid flanked by the primers duplexed with their complementary segments. The amplified nucleic acid is then contacted with a nucleic acid polymerase having a 3' to 5' exonuclease activity and one or more nucleobase units in solution. The polymerase with exonuclease activity digests at least parts of the amplified nucleic acid complementary to the 5' segments of the primers, and the amplified nucleic acid circularizes via annealing of the 5' segments. The nucleobase units in solution can be characterized as being of a type different than the digested nucleobase units of the parts of the amplified nucleic acid complementary to the 5' segments. The circularized nucleic acid with a ligase which seals a nick between the 5' phosphate group of the first primer and an adjacent 3' hydroxyl group leaving the circularized template with a single nick or gap between the 5' segment of the second primer and a 3' hydroxyl of an adjacent nucleotide. The invention also provides methods of forming a circular template for sequencing a target nucleic acid. These methods comprising contacting a target nucleic acid with a primer pair under PCR conditions, each of the primers having a 3' segment and a 5' segment, the 3' segments of the primers being target-binding segments, the 5' segments being mutually complementary in opposing orientations, a first of the primers having a 5' phosphate group and the second of the primers lacking a 5' phosphate and/or having a shorter 5' segment than the first primer; thereby forming an amplified nucleic acid comprising a segment of the target nucleic acid flanked by the primers duplexed with their complementary segments. The amplified nucleic acid is then contact with a nucleic acid polymerase having a 3' to 5' exonuclease activity and one or more nucleobase units in solution. The nucleobase units in solution are of a type different than the nucleobase units complementary to the nucleobases in the 5' segments of the primers. The polymerase with exonuclease activity digests at least parts of the amplified nucleic acid complementary to the 5' segments of the primers, and the amplified nucleic acid circularizes via annealing of the 5' segments. The circularized nucleic acid is then with a ligase which seals a nick between the 5' phosphate group of the first primer and an adjacent 3' hydroxyl group leaving the circularized template with a single nick or gap between the 5' segment of the second primer and a 3' hydroxyl of an adjacent nucleotide.

In some of the above methods, each primer further comprises a cushion segment between the 5' segment and the 3' segment, the cushion segment including at least one nucleobase unit complementary to a type of the one or more nucleobase units in solution, whereby the exonuclease digestion terminates at or in the complements of the cushion segments in the amplified nucleic acid. In some such methods, the cushion segment nucleobase unit(s) consist of a single type of canonical nucleobase unit, and the 5' segment nucleobase units are the two canonical nucleobase types other than the single type of canonical nucleobase and its complement except that if one 5' segment is longer than the other, the extra portion of the longer 5' segment may contain the single type of canonical nucleobase unit. In some such methods, the cushion segment nucleobase units consist of two types of canonical nucleobase units complementary to one another and the 5' segments nucleobase units consist of the other two types of canonical nucleobase unit. In some such methods, the nucleobase units of the cushion region consist of A, or T/U, or A and T/U, and the nucleobase units of the 5' regions consist of C and G. In some such methods, the nucleobase units of the cushion region consist of C or G, or C and G, and the nucleobase units of the 5' regions consist of A and T/U.

In some such methods, a 5' segment or cushion segment of the first and/or second primer includes one or more noncanonical nucleobase units. In some such methods, all nucleobase units in the primer are canonical nucleobase units.

In some such methods, the target nucleic acid is a genomic DNA molecule, a cDNA molecule or an RNA molecule.

In some such methods, the nucleic acid polymerase is a DNA polymerase, such as a T4 DNA polymerase. In some methods, the ligase is a DNA ligase, such as a T4 DNA ligase. In some methods, the ligase is a RNA ligase. In some methods, the ligase is a thermophilic DNA ligase and step (c) is performed at a temperature over 40 degrees.

In some methods, the 5' segment of the first primer is longer than the 5' segment of the second primer resulting in a gap between the 5' end of the second primer and a 3' hydroxyl of an adjacent nucleotide in the amplified nucleic acid. In some methods, the 5' segment of the first primer is longer than the 5' segment of the second primer by four nucleobase units and the gap is four nucleobase units.

In some methods, contacting steps (b) and (c) are performed at the same time. In some methods, the PCR conditions including at least ten thermocycles. In some methods, each of the primers has a 5' segment of at least 5 nucleobase units. In some methods, each of the primers has a 3' segment of at least 10 nucleobase units.

The invention further provides methods for sequencing a target nucleic acid. Such methods include: (a) contacting a double-stranded circularized template with a polymerase and nucleobase units, wherein the template comprises a target nucleic acid segment and a single nick or gap in one of its strands; and (b) conducting template directed-extension from a free 3'-hydroxyl of a nucleobase unit abutting the nick or gap directed by the circular template incorporating the nucleobase units into a nascent chain including multiple copies of the same strand of the target nucleic acid segment; and detecting the incorporation of nucleobase units into the nascent chain to determine the sequence of the strand of the target nucleic acid segment.

In some such methods, the incorporation of a nucleobase unit is detected after its incorporation and before incorporation of the next nucleobase unit. In some such methods, the nick or gap is not within the target nucleic acid segment of the circularized template before beginning the template-directed extension. In some such methods, the target nucleic acid segment is of unknown sequence and the remainder of the circular template is of known sequence and the nascent chain includes alternating copies of the target segment and the known sequence.

In some such methods, the nick or gap is a gap of 1-20 nucleobase units. In some such methods, the nick or gap is a nick.

The circularized template is the above methods can be generated by any of the methods disclosed above and herein or otherwise.

In some of the above methods, the target nucleic acid a human genomic DNA segment. For example, the target nucleic acid can be biallelic with the target nucleic acid segment including the polymorphic site(s) conferring biallelism. The target nucleic acid can be from an individual heterozygous for the bialleles. The target nucleic acid can be a population of variant nucleic acids including at least one minority species and a majority species, such as a population of HIV or HCV nucleic acids.

In some of the above methods, the incorporation of nucleobase units into the nascent chain is detected by measuring the presence of a label on the nucleobase units being incorporated. In some of the above methods, the label is a fluorescent label. In some of the above methods, the incorporation of nucleobase units into the nascent chain is detected by measuring the release of a label from the nucleobase units being incorporated. In some of the above methods, the label is a fluorescent label. In some of the above methods, the incorporation of nucleobase units into the nascent chain is detected by measuring a chemical change that occurs during the incorporation of the nucleobase units, for example, a release of a proton, a change in energy, a release of a pyrophosphate from the nucleobase units, or a combination thereof. In some of the above methods, the detecting is single-molecule real-time detecting. In other methods, the methods are performed on a plurality of circularized templates and incorporation of consensus nucleobases into nascent chains formed from the plurality of circularized templates is detected to determine a consensus sequence of a target nucleic acid segment in the plurality of circular templates.

The above methods can be performed on a plurality of circular template molecules containing target nucleic acid segments from different variants of a target nucleic acid to determine the sequences of strands of different variants of the target nucleic acid.

The invention further provides a kit comprising a pair of primers, each of the primers having a 3' segment and a 5' segment, the 3' segments of the primers being target-binding segments, the 5' segments being mutually complementary in opposing orientations, a first of the primers having a 5' phosphate group and the second of the primers lacking a 5' phosphate and/or having a shorter 5' segment than the first primer. The kit can also contain a polymerase with 3'-5' exonuclease activity; and a ligase.

The invention further provides for the use of a pair of primers, each of the primers having a 3' segment and a 5' segment, the 3' segments of the primers being target-binding segments, the 5' segments being mutually complementary in opposing orientations, a first of the primers having a 5' phosphate group and the second of the primers lacking a 5' phosphate and/or having a shorter 5' segment than the first primer, a polymerase with 3'-5' exonuclease activity; and a ligase to make a circular template having a single nick or gap.

Definitions

A nucleic acid refers to a multimeric compound comprising nucleotides or analogs that have nitrogenous heterocyclic bases or base analogs linked together to form a polymer, including conventional RNA, DNA, mixed RNA-DNA, and analogs thereof.

The nitrogenous heterocyclic bases can be referred to as nucleobases. Nucleobases can be conventional DNA or RNA bases (A, G, C, T, U), base analogs, e.g., inosine, 5-nitroindazole and others (The Biochemistry of the Nucleic Acids 5-36, Adams et al., ed., 11.sup.th ed., 1992; van Aerschott et al., 1995, Nucl. Acids Res. 23(21): 4363-70), imidazole-4-carboxamide (Nair et al., 2001, Nucleosides Nucleotides Nucl. Acids, 20(4-7):735-8), pyrimidine or purine derivatives, e.g., modified pyrimidine base 6H,8H-3,4-dihydropyrimido[4,5-c][1,2]oxazin-7-one (sometimes designated "P" base that binds A or G) and modified purine base N6-methoxy-2,6-diaminopurine (sometimes designated "K" base that binds C or T), hypoxanthine (Hill et al., 1998, Proc. Natl. Acad. Sci. USA 95(8):4258-63, Lin and Brown, 1992, Nucl. Acids Res. 20(19):5149-52), 2-amino-7-deaza-adenine (which pairs with C and T; Okamoto et al., 2002, Bioorg. Med. Chem. Lett. 12(1):97-9), N-4-methyl deoxygaunosine, 4-ethyl-2'-deoxycytidine (Nguyen et al., 1998, Nucl. Acids Res. 26(18):4249-58), 4,6-difluorobenzimidazole and 2,4-difluorobenzene nucleoside analogues (Kiopffer & Engels, 2005, Nucleosides Nucleotides Nucl. Acids, 24(5-7) 651-4), pyrene-functionalized LNA nucleoside analogues (Babu & Wengel, 2001, Chem. Commun. (Camb.) 20: 2114-5; Hrdlicka et al., 2005, J. Am. Chem. Soc. 127(38): 13293-9), deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methylaminopurine, O-6-methylguanine, 4-thio-pyrimidines, 4-amino-pyrimidines, 4-dimethylhydrazine-pyrimidines, and O-4-alkyl-pyrimidines (U.S. Pat. No. 5,378,825; PCT No. WO 93/13121; Gamper et al., 2004, Biochem. 43(31): 10224-36), and hydrophobic nucleobases that form duplex DNA without hydrogen bonding (Berger et al., 2000, Nucl. Acids Res. 28(15): 2911-4). Many derivatized and modified nucleobases or analogues are commercially available (e.g., Glen Research, Sterling, Va.).

A nucleobase unit attached to a sugar, can be referred to as a nucleobase unit, or monomer. Sugar moieties of a nucleic acid can be ribose, deoxyribose, or similar compounds, e.g., with 2' methoxy or 2' halide substitutions. Nucleotides and nucleosides are examples of nucleobase units.

A canonical nucleobase unit refers to the four types of nucleobase units commonly found in natural DNA or RNA or their corresponding triphosphates. In DNA, the four canonical nucleobase units are deoxyribo-adenine, cytosine, guanine, and thymine. In RNA, the four canonical nucleobase units are ribo-adenine, cytosine, guanine or uracil. If a nucleic acid is referred to generically (i.e., including DNA and RNA), the four canonical nucleobase units are adenine, cytosine, guanine and thymine/uracil. Thymine/uracil means thymine in the context of a DNA molecule and uracil in the context of an RNA molecule.

A non-canonical nucleobase unit is a nucleobase unit other than a canonical nucleobase unit. A non-canonical nucleobase unit should support template-directed incorporation of a complementary nucleobase unit, which can be canonical or non-canonical.

Examples of non-canonical nucleobase unit include methylated nucleobase units, which refer to nucleobase units that carry a methyl group attached to a position of a nucleobase unit that is accessible for methylation. Examples of methylated nucleobase units include methyl dCTP, methyl dGTP, methyl dATP and methyl dTTP.

A non-canonical nucleobase unit pair refers to a pair of non-canonical nucleobase units that base pairs with each other but do not base pair or base pair less strongly with canonical nucleobase units A, C, G, and T/U. Examples of non-canonical nucleobase unit pairs include isocytosine (isoC) and isoguanine (isoG) (U.S. Pat. Nos. 5,432,272, 6,001,983, 6,037,120, 6,104,0496, 6,617,106, 6,977,161; U.S. Patent Application Nos. 20040106108, 20060078936; EP1358352, EP1590482, WO0233126 and WO04065550), 5-methylisocytosine and isoguanine; Im-N$^O$ and Im-O$^N$; A* and T*; and 8-oxoG and adenine. Other non-canonical nucleobase unit pairs include but are not limited to 2,4-diamino-5-(β-D-2'-deoxyribofuranosyl)pyrimidine (dκ) and deoxyxanthosine triphosphate (dX) (Horlacher et al. PNAS USA 1995; 92:6329-6333; Piccirilli et al. Nature 1990; 343:33-37); 2,4-diaminopyrimidine (pyDAD) and xanthine (puADA) (Sismour et al. Nucleic Acids Res. 2004; 32:728-735). Some non-canonical bases may require the use of modified polymerase to facilitate their efficient incorporation into amplicons.

The nucleobase units can be joined by a variety of linkages or conformations, including phosphodiester, phosphorothioate or methylphosphonate linkages, peptide-nucleic acid linkages (PNA; Nielsen et al., 1994, Bioconj. Chem. 5(1): 3-7; PCT No. WO 95/32305), and a locked nucleic acid (LNA) conformation in which nucleotide monomers with a bicyclic furanose unit are locked in an RNA mimicking sugar conformation (Vester et al., 2004, Biochemistry 43(42):13233-41; Hakansson & Wengel, 2001, Bioorg. Med. Chem. Lett. 11 (7):935-8), or combinations of such linkages in a nucleic acid strand. Nucleic acids may include one or more "abasic" residues, i.e., the backbone includes no nitrogenous base for one or more positions (U.S. Pat. No. 5,585,481).

A nucleic acid may include only conventional RNA or DNA sugars, bases and linkages, or may include both conventional components and substitutions (e.g., conventional RNA bases with 2'-O-methyl linkages, or a mixture of conventional bases and analogs). Inclusion of PNA, 2'-methoxy or 2'-fluoro substituted RNA, or structures that affect the overall charge, charge density, or steric associations of a hybridization complex, including oligomers that contain charged linkages (e.g., phosphorothioates) or neutral groups (e.g., methylphosphonates) may affect the stability of duplexes formed by nucleic acids.

Complementarity of nucleic acids means that a nucleotide sequence in one strand of nucleic acid, due to orientation of its nucleobase groups, hydrogen bonds to another sequence on an opposing nucleic acid strand. The complementary bases typically are, in DNA, A with T and C with G, and, in RNA, C with G, and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" refers to the cumulative environment in which one nucleic acid strand bonds to a second nucleic acid strand by complementary strand interactions and hydrogen bonding to produce a hybridization complex.

Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment (e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989)).

A "label" refers to a molecular moiety that is detectable or produces a detectable response or signal directly or indirectly, e.g., by catalyzing a reaction that produces a detectable signal. Labels include luminescent moieties (such as fluorescent, bioluminescent, or chemiluminescent compounds), radioisotopes, members of specific binding pairs (e.g., biotin and avidin), enzyme or enzyme substrate, reactive groups, or chromophores, such as a dye or particle that results in detectable color.

A "primer" is an oligonucleotide, typically between about 10 to 100 nucleotides in length, capable of selectively binding to a specified nucleic acid or "template" by hybridizing with the template. The primer provides a point of initiation for polymerase-mediated template-directed synthesis of a nucleic acid complementary to the template. Primers hybridizing to opposing strands of a double-stranded sequence are referred to as forward and reverse primers.

An oligonucleotide primer used to initiate a sequencing reaction is referred to as a sequencing primer.

A "copy" of a particular nucleic acid segment, such as generated by multiple passes around a circular template, can mean an exact copy or a substantially similar copy (e.g., greater than 80% sequence identity) due to occasional sequencing errors, such as misincorporation of noncomplementary nucleobase(s) or misidentification of incorporated nucleobase(s).

DETAILED DESCRIPTION OF THE INVENTION

1. General

Figure 2:
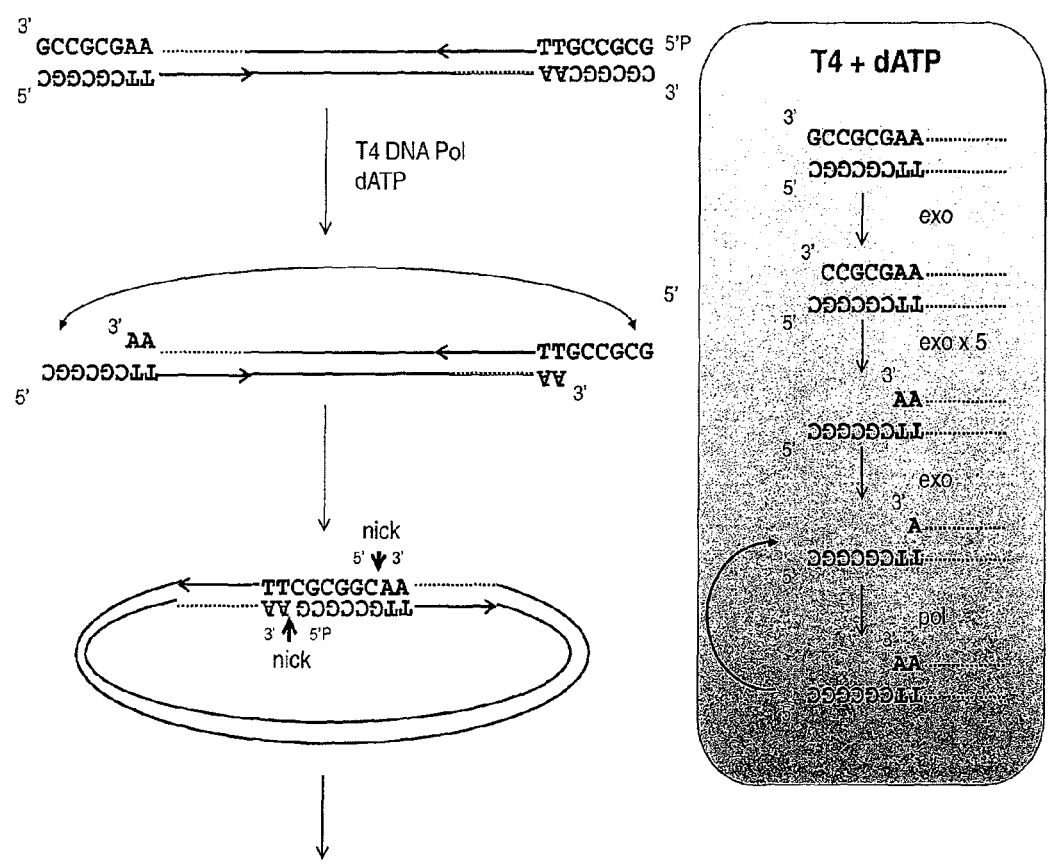
Figure 3:
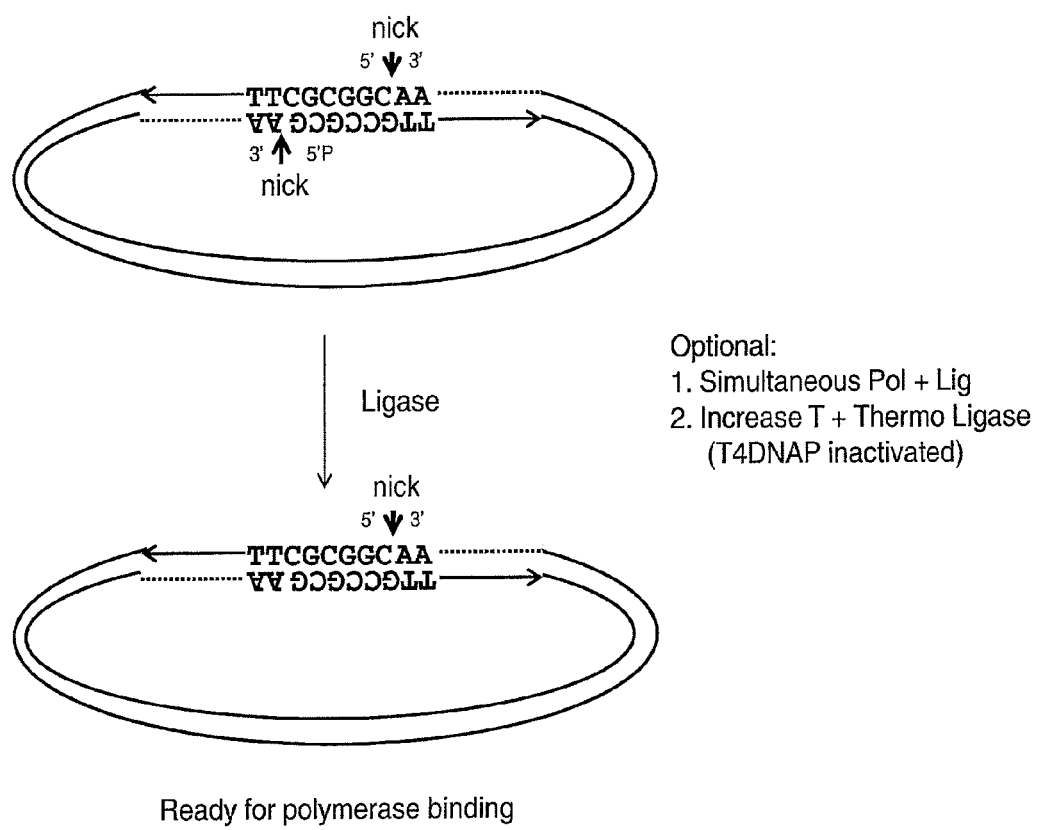

The present invention provides methods of generating a circularized template useful for sequencing a target nucleic acid. An exemplary form of the methods is shown in FIGS. 1-3. A target nucleic acid is subjected to cycled primer extension reactions, such as in polymerase chain reaction (PCR), or to isothermal primer extension reactions, such as in transcription mediated amplification reactions (TMA), using a pair of primers having a 5' segment, a 3' segment, and optionally a cushion segment between the 5' and 3' segments, as exemplified by FIG. 1 (the cushion segment is represented by TT). One of the primers has a 5' phosphate group. The primers hybridize to opposing strands of the target nucleic acid and amplification with the primers results in a linear amplification product in which a segment of the target nucleic acid is flanked by the primers duplexed with their complementary segments (lower part of FIG. 1). The number of cycles in a PCR-like cycled extension reaction can be the minimum number of cycles needed to incorporate both primers into the product, or can be many cycles to cause amplification of the product containing the incorporated primers. Regardless of the number of cycles, any product of such a reaction incorporating a target nucleic acid and the primers is referred to as an amplicon or an amplification product. The amplification product is then digested with a nucleic acid polymerase with 3' to 5' exonuclease activity in the presence of nucleobase unit(s) of types absent from the 5' segments and/or their complements. More preferably, the amplification product is then digested with a nucleic acid polymerase with 3' to 5' exonuclease activity in the presence of nucleobase unit(s) of types absent from the complements of the 5' segments. The exonuclease activity of the polymerase digests at least some of the complements of the 5' segments of the primers. The exonuclease digestion terminates on reaching a position having one of the nucleobase units present in the digestion reaction, which can be located in the complement of a cushion segment or in the target nucleic acid segment (see FIG. 2, showing termination when exonuclease digestion reaches the first A of the complement of a cushion segment). After exonuclease digestion, the amplified product has mutually complementary overhanging 5' segments (i.e., sticky ends). The amplified nucleic acid circularizes via annealing of the overhanging 5' segments (FIG. 2, lower). The 5' phosphate on one of the primers is ligated to an adjacent 3' hydroxyl group leaving a single nick or gap in the circularized nucleic acid between the other 5' primer end and an adjacent 3' hydroxyl (FIG. 3). This 3'-hydroxyl serves as a priming end to initiate template-directed synthesis of a nascent chain in circles around the template generating alternating reads of primer segments and the target nucleic acid. Because the circular template contains only one priming site, only one strand of the target nucleic acid is read from a given template. Because only one strand of the target nucleic acid is sequenced per reaction, the present method avoids errors introduced by unwittingly combining sequence reads of both strands of a heteroduplex PCR product.

II. Primers

The present methods employ a pair of forward and reverse primers hybridizing to opposing strands of a target nucleic acid (if double-stranded) or to a target nucleic acid and its complementary strand, if the target nucleic acid is single-stranded. Both primers include, in 5' to 3' direction, a 5' segment and a 3' segment. The 3' segments are target-binding segments that are complementary to the target nucleic acid (as is the case for conventional PCR primers). Exemplary lengths for the 3' segments are at least 5, 10, 15 or 20 nucleobases units and optionally up to 30, 40 or 50 including all permutations of upper and lower limits. The spacing of the primers with respect to the target nucleic acid defines a segment of the target nucleic acid that is amplified and available for sequencing.

The 5' segments are mutually complementary to one another in opposing orientations to permit annealing of nucleic acids via the 5' segments. This means that the 5' segments have sufficient complementarity to permit circularization via annealing but does not preclude, for example, one 5' segment from having one (or more) extra segment(s) not represented in the other 5' segment as discussed further below. To illustrate for 5' segments of the same length and showing perfect complementarity to one another, a 5' segment of a first primer having the sequence of 5'-GCGCCG-3' is complementary to the 5' segment of a second primer having the sequence of 5'-CGGCGC-3'. The 5' segments and their complements can be designed so that nucleobase units to be digested from the complements of the 5' segments in a subsequent step are different from nucleobase units supplied to a polymerase with 3'-5' exonuclease activity. A preferred design is for the 5' segments to include two and only two of the four canonical nucleobase units. For example, the nucleobase units in the 5' segments and their complements can be all G or C, or all A or T/U. The 5' segments can also include one or more noncanonical nucleobase units as well as instead of one or both of the two canonical nucleobase units. Usually, if one or more noncanonical nucleobase units are used, they are used in combination with two canonical nucleobase units.

The 5' segments have a length sufficient to permit annealing to form a circular template as further described below, preferably under the same or similar conditions as employed for exonuclease digestion and ligation, which is often at a moderate temperature of e.g., 12-37° C. Preferably the 5's segments are not so long as to permit substantial annealing between 5' segments under the higher temperature conditions of amplification so that the predominant amplification product is a segment of the target nucleic acid. Typically the lengths are at least 2, 3, 4, 5, 6, 8, 10 or 15 nucleobase units and optionally up to 6, 10, 15 or 20, nucleobase units including all permutations of upper and lower limits in which the lower limit is lower than the higher limit.

The 5' segments can have the same or different lengths. If of different lengths, the extra portion of one 5' segment that has no complement in the other 5' segment is preferably adjacent to the cushion segment or the 3' segment if no cushion is used. The nucleobase composition of the extra portion has more flexibility than that of the rest of the 5' segment because there is no corresponding complementary portion in the 5' segment from the other primer. To allow digestion of the complement of the extra portion, it should contain nucleobases of a different type than the nucleobase units in solution. Therefore, if for example, only a single canonical nucleobase unit is used in solution, that type of nucleobase unit plus the other two types of nucleobase units noncomplementary to this nucleobase unit can be used in the extra portion of one of the 5' segments. Accordingly, the complement of the extra portion does not contain the single canonical nucleobase type used in solution.

If the 5' segments have different lengths, a circular template incorporating primers of unequal lengths has a gap between the 5' segment of shorter length and an adjacent 3' hydroxyl group. The length of this gap is the number of nucleobase units different in length between the 5' ends. The width of the gap can be chosen depending on several considerations, e.g., the preferences of the sequencing polymerase. For example, the difference in length can be e.g., at least 1, 2, 3, 4 or 5 nucleobase units and optionally up to 20 nucleobase units including all permutations of the lower and upper limits generating a gap of the same length. Preferably, the 5' segment of the first primer is longer than the 5' segment of the second primer by four nucleobase units and the gap is four nucleobase units. Larger gaps for example ranging up to ¾ the length of the ungapped strand can also be made with exonuclease digestion after forming a nicked or gapped template as discussed further below. In some circular templates, the gap is ¼ to ¾ the length of the intact circularized strand.

One and usually only one of the primers has a 5' phosphate group. This primer is arbitrarily referred to as the first primer, and the other primer as the second primer. If the 5' segments of the primers are of unequal length, the shorter 5' segment is included in the second primer. Typically, the second primer does not have a 5' phosphate regardless of whether its 5' segment is the same or shorter than that of the first primer because the intention is to leave a nick or gap adjacent this 5' end. However, if a 5' segment of the second primer is shorter than that of the first primer resulting in a gap next to the 5' end in the circularized template, the 5' end of the second primer can have a phosphate group because ligation acts to close a nick but not a gap.

Preferably, one or, more preferably both primers include a cushion segment between the 5' segment and the 3' segment. The nucleobase unit(s) in the cushion segment are preferably of type(s) different than the nucleobase units in the 5' segments and their complements. Usually, the nucleobase units in the cushion segments are a single type of canonical nucleobase unit or two complementary types of canonical nucleobase units. For example, if the nucleobase units in the 5' segments and their complements are G and C, then the nucleobase units in the cushion segments can be A only, or T/U only, or both A and T/U. Conversely, if the nucleobase units in the 5' segments and their complements are A and T/U, then the nucleobase units in the cushion segments can be C only, G only, or G and C. The cushion segment can be a homo-oligomeric segment (containing a single type of nucleobase) or a hetero-oligomeric segment. Examples of homo-oligomeric cushion segments include 5'-G-G-3', 5'-T-T-T-3', and 5'-C-C-C-C-3'. Some cushion segments are a hetero-oligomeric segment of two complementary canonical nucleobase units. For example, the cushion segment can have one or more A and T, or one or more C and G. Optionally, one or more non-canonical nucleobase units can be included in the cushion segments, as well as or instead of one or both of the canonical nucleobase types included. The cushion segments are intended to terminate exonuclease digestion as further described below. Cushion segments can sometimes contain at least 1, 2, 3, 4, 5, or 6 nuclease base units, and optionally up to 10 nucleobase units including all permutations of lower and upper limits. Preferably cushion segments have 4-6 nucleobase units.

The cushion segments can be of the same or different lengths including a design in which one primer has a cushion segment and the other does not.

Optionally, primers can further include a barcode segment, for example, embedded in a pattern of a 5' segment or a cushion segment. Bar codes are differentiable sequences useful for identifying the origin of particular target segment. Bar codes are useful for sequencing pooled samples. For example, samples from two different sources can be independently amplified using primers having a unique barcode segment for each sample from a source. The amplified samples are then pooled and sequenced in a combined reaction. The unique sequences of the barcode segments identify the source of each sequenced sample.

III. Amplification

The target nucleic acid is contacted with the primer pair under conditions suitable for amplification, usually but not necessarily by the polymerase chain reaction PCR. Suitable PCR conditions include a suitable buffer, polymerase, nucleobase units for incorporation and thermocycling. Exemplary conditions use 2-50 cycles each cycle including a denaturing step (e.g. 10 seconds at 94° C.), an annealing step (e.g. 15 sec at 68° C.), and an extension step (e.g. 1 minute at 72° C.). The number of cycles can be at least 1, 2, 5, 10, 20, 30, 50 thermocycles but is sometimes less than conventional PCR (e.g., between 2, 3, 4 to 5 on the lower end and 10, 15 or 20 cycles on the upper end including any permutation of upper and lower limits).

PCR is described by (U.S. Pat. Nos. 4,683,195, 4,683,202, 4,800,159 and 4,965,188, commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and U.S. Pat. No. 4,800,159; Mullis et al., *Meth.*

Enzymol. 155: 335 (1987); and, Murakawa et al., *DNA* 7: 287 (1988). For example, the target is RNA it can first be converted to DNA by RT-PCR. An RNA target can also be directly amplified in a PCR reaction or cycled primer extension reaction using a RNA-directed DNA polymerase such as Tth DNA polymerase.

Other amplification techniques that can be used include transcription-mediated amplification (TMA), ligase chain reaction (LCR), strand displacement amplification (SDA), and nucleic acid sequence based amplification (NASBA). Whereas PCR reverse transcribes RNA to DNA prior to amplification (e.g., RT-PCR), TMA and NASBA can directly amplify RNA.

Transcription mediated amplification (U.S. Pat. Nos. 5,480,784 and 5,399,491), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518. In a variation described in U.S. Publ. No. 20060046265, TMA optionally incorporates the use of blocking moieties, terminating moieties, and other modifying moieties to improve TMA process sensitivity and accuracy.

Strand displacement amplification (Walker et al., *Proc. Natl. Acad. Sci. USA* 89: 392-396 (1992); U.S. Pat. Nos. 5,270,184 and 5,455,166,), commonly referred to as SDA, uses cycles of annealing pairs of primer sequences to opposite strands of a target sequence, primer extension in the presence of a dNTPs to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

The ligase chain reaction (Weiss, *Science* 254: 1292 (1991) commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Other amplification methods include, for example: nucleic acid sequence based amplification (U.S. Pat. No. 5,130,238), commonly referred to as NASBA; one that uses an RNA replicase to amplify the probe molecule itself (Lizardi et al., *BioTechnol.* 6: 1197 (1988, commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990). For further discussion of known amplification methods see Persing, "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

If an amplification technique other than PCR is used, standard conditions including a polymerase, nucleobase units, and buffer for such other technique can be used.

IV. Exonuclease Reaction

The amplification product is a linear product in which a target nucleic acid segment is flanked by the primers duplexed with complementary sequences (see, g., FIG. 1, lower). After amplification, the amplification product is preferably separated from any remaining nucleobase units from the amplification.

The amplified nucleic acid is treated with a nucleic acid polymerase having a 3'-5' exonuclease activity and one or more nucleobase units that are preferably of types absent from the 5' primer segments and/or their complements. More preferably, the nucleobase units in solution are absent from the complements of the 5' primer segments. As mentioned above, if one 5' segment contains an extra portion for which there is no extra complementary segment in the other primer, there is additional flexibility in design of this extra portion. The extra portion may contain a nucleobase unit type used in solution but the complement of the extra portion preferably does not to allow complete digestion of the complement.

If one or more primers with a cushion segment is used, the nucleobase units provided to the polymerase are usually complementary to the nucleobase types included in the cushion. For example, if the cushion consists of A nucleotides, only a T/U nucleotide can be provided to the polymerase. If the cushion consists of A and T/U nucleotides, either A or T/U or both A and T/U can be provided to the polymerase. Preferably, the nucleobase unit provided to the polymerase is a single type of canonical nucleobase unit or two types of complementary canonical nucleobase units.

The exonuclease activity of the nucleic acid polymerase digests at least parts (one part on each strand) of the amplified nucleic acid complementarity to the 5' segments of the primers (see, e.g., FIG. 2, middle). Preferably the nuclease activity digests the entire parts complementary to the 5' segments of the primers. When the primers contain a cushion segment (as in FIG. 2), the exonuclease activity digests the complements of the 5' segments, and terminates at (i.e., immediately before the first nucleobase unit of the cushion) or in the complements of the cushion segments in the amplified nucleic acid. When the primers do not contain a cushion segment, the exonuclease digestion terminates in the target region at a position having a nucleobase unit of the same type as is supplied with the polymerase.

Digestion of a nucleobase unit from a nucleic acid by a polymerase with 3'-5 nuclease activity means that the nucleobase unit is cleaved and not replaced by a nucleobase unit of the same type present in solution. A nucleobase unit that is transiently removed only to be replaced by a nucleobase unit of the same type resulting in the same template molecule as before the transient removal is not considered to have been digested.

The exonuclease activity leaves a linear molecule with overhanging 5' ends as shown in the lower portion of FIG. 2. The linear molecule can then be circularized via annealing of the overhanging 5' segments. Annealing may occur spontaneously. If desired, the stringency of the annealing conditions and the concentrations of the nucleic acid can be adjusted to improve the yield of the circularized nucleic acid (see, e.g., Sambrook et al., 1989, Molecular Cloning: A Laboratory Manual, Cold Spring Harbor Laboratory, New York).

Nucleic acid polymerase is an enzyme that is capable of, in a template dependent manner, elongating at least one strand of nucleotides, e.g., a polynucleotide, by sequentially incorporating single nucleotides, typically, in a 5' to 3' direction. Nucleic acid polymerases include both DNA (DNA dependent DNA polymerases; RNA dependent DNA polymerases or reverse transcriptases) and RNA polymerases (DNA dependent RNA polymerases; RNA dependent RNA polymerases). 3' to 5' exonuclease or 3' to 5' exonuclease activity refers to a protein or domain of a protein that catalyzes the stepwise removal of mononucleotides from 3'-termini of DNA molecules, i.e., cleaving bonds, preferably phosphodiester bonds, between nucleotides one at a time from the end of a DNA molecule.

When a DNA template is used, a variety of DNA polymerases with 3' to 5' exonuclease activity can be used. At least five families of DNA-dependent DNA polymerases are known, although most fall into families A, B and C. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. Accordingly, A-type, B-type, and C-type polymerases having 3' to 5' exonuclease activity can be used in the present method. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases.

Thermostable or non-thermostable polymerases can be used. Examples of thermostable polymerase having 3' to 5' exonuclease activity include *Pyrococcus* polymerases e.g., Pfu, Pwo, Pho, Pab, Pko, Pgl polymerases; *Thermococcus* polymerases, e.g., *Thermococcus litoralis*, *Thermococus barossii*, and *Thermococcus gorgonarius* polymerases; and polymerases from *Pyrodictium* sp. Thermostable polymerases having 3' to 5' exonuclease activity can also be isolated from eubacterial strains such as *Thermotoga*. Non-thermostable polymerases can also be used. Examples of non-thermostable polymerases include the large fragment of *E. coli* DNA Polymerase I (Klenow) has 3' to 5' exonuclease activity. Preferably, a T4 DNA polymerase is used.

A nucleic acid polymerase with 3' to 5' exonuclease activity can be a hybrid protein comprising amino acid residues from multiple parent sequences. Examples of hybrid polymerase proteins and methods of generating hybrid proteins are disclosed in WO2004011605. Such polymerases are therefore non-naturally occurring variants of polymerases.

Appropriate conditions for digesting with a polymerase with 3' to 5' exonuclease activity are described by e.g., Maniatis et al. Molecular Cloning—a Laboratory Manual; Cold Spring Harbor Laboratory Press First Edition (1989), p. 135).

V. Ligation

The circularized nucleic acids contains nicks or gaps between the 5' primer ends and adjacent hydroxyl groups (see, e.g., FIG. 2, lower). The nick in one strand of the circularized nucleic acids can be ligated using a nucleic acid ligase (see, FIG. 3). The ligase joins a 5' phosphate group from the first primer to an adjacent hydroxyl. A nick or gap between the 5' end of the second primer and a 3' hydroxyl is not sealed because the second primer does not have a 5' phosphate group (see FIG. 3) and/or there is a gap between the 5' end of the second primer and an adjacent 3' hydroxyl due to the 5' ends of the primers being of unequal length (see FIGS. 4 and 5).

The polymerase 3'-5' exonuclease and ligase reactions can be performed sequentially (exonuclease first) or both enzymes can be supplied together so that once the exonuclease digestion is complete the digested nucleic acids can be annealed. In some cases, a thermophilic nucleic acid ligase and a non-thermophilic polymerase can be used. Once the digestion is complete, the temperature can be (but need not be) increased, e.g., over 40, 50, 60, or 70° C. to inactivate the polymerase, whereas the thermophilic ligase remains active at the elevated temperature. An additional or alternate heat inactivation can carried out after both exonuclease digestion and ligation are complete and before sequencing.

As an alternative to using 5' ends of unequal length to generate a gap, a gap can be generated by digesting at the remaining nick in the circular template after ligation. For example, after completing ligation, nucleobase unit(s) used in the previous polymerase 3'-5' digestion can be purified away and fresh polymerase with 3' to 5' exonuclease activity and one or more different nucleobase units are added. The exonuclease activity then digests through the complement of the cushion segment 5' segment and stops when the first nucleobase unit in the target segment of the same type as a now-supplied nucleobase unit is encountered. Alternatively, any exonuclease with 3' to 5' activity can be used to remove nucleobase units from the 3' end of the complement of the cushion possibly extending into the target segment. The amount of digestion can be controlled by using a short time or limited amount of exonuclease.

Alternatively, an exonuclease with 5' to 3' activity can be used to initiate digestion at a nick or gap that was introduced according to the present methods. For example, after completing ligation, and optionally inactivating the polymerase with 3'-5' exonuclease activity and the ligase, and removing nucleobase unit(s) used in the previous polymerase 3'-5' digestion, an exonuclease with 5' to 3' exonuclease is added. The exonuclease activity then digests from the 5' end of the second primer and possibly through the cushion segment and into the target segment. The amount of digestion can be controlled by using a short time or limited amount of exonuclease or using 5' primer segments with modified nucleobase units or backbone bonds that resist exonuclease digestion.

The ligated nucleic acid product can be purified to remove linear nucleic acids or other impurities and undesired side products. Because the ligated nucleic acids have a compact structure and a size smaller than undesired side products, they can be readily purified using standard methods such as gel purification or affinity chromatography.

A variety of ligases can be used. Nucleic acid ligases are a family of enzymes which catalyze the formation of a covalent phosphodiester bond between two distinct nucleic acid strands, i.e. a ligation reaction. Examples of nucleic acid ligases include DNA ligases and RNA ligases. A DNA ligase means any protein or peptide, of synthetic, recombinant or natural origin, exhibiting a DNA ligase activity, i.e., catalyzing the formation of a covalent phosphodiester bond between two distinct DNA strands. Examples of DNA ligases include the ATP-dependent T4 DNA ligase (isolated from the T4 phage) and the NAD$^+$-dependent DNA ligase from *E. coli*. Both enzymes catalyze the synthesis of a phosphodiester bond between the 3'-hydroxyl group of one nucleic acid strand, and the 5'-phosphoryl group, of a second nucleic acid strand, for instance at a nick between the two strands which are both hybridized to a third DNA strand. RNA ligases, which are a related family of enzymes, catalyze the ligation of nicked RNA ends hybridized on to RNA or DNA in an analogous fashion.

Thermostable or non-thermostable ligases can be used. DNA ligases useful for the present method also include natural DNA ligases or fragments, derivatives or analogues with at least 90%, 95%, or 98% identity to a natural DNA ligase, such as an *E. coli* DNA ligase, a DNA ligase from thermophilic bacteria, e.g., ligases from the genus *Thermus* including ligases from *T. aquaticus, T. thermophiles, T. rubber, T. filiformis, T. brockianus, T. flavus* and *T. scotoductus*. When a thermophilic DNA ligase is used, the ligation can be performed at a temperature, e.g., over 40, 50, 60, or 70 degrees.

VI. Sequencing

A double-stranded circular template including a target acid segment and with a single nick or gap as generated by the above methods or otherwise is suitable for sequence analysis of the target nucleic acid. In contrast to SMRTbell template sequencing, the methods can be performed by initiating template extension and thus sequencing without a sequencing primer other than the template itself. In some methods, the nick or gap is no more than 20 nucleobase units long. In some methods, the nick or gap is up to ¼ or ½ the length of the complete strand. The template is contacted with a polymerase and nucleobase units. Sequencing is performed by template-directed extension starting from a free 3' hydroxyl of the circularized template, such as shown in the lower portion of FIG. 3 or FIG. 6. The extension is directed by the circular template and incorporates supplied nucleobase units into a nascent chain. Extension initiated at the free 3'-hydroxyl can proceed around the circular template and can continue around the circle multiple times generating alternating copies of a strand of the target nucleic segment and a portion of the template other than the target segment, which usually provides the location at which the nick or gap is initially present. The nick or gap moves around the circle as extension from the 3'-hydroxyl at the nick or gap occurs. The target nucleic acid segment is usually of unknown sequence and the rest of the template, which can originate from the primers in the present methods, is usually of known sequence.

The sequencing can be in real-time or non-real time. Real-time sequencing means that incorporated nucleobase units can be detected contemporaneous with incorporation (i.e., before a subsequent nucleobase unit is incorporated). Alternatively sequencing can be non-real time meaning that incorporated nucleobase units are detected after formation of a nascent chain or at least after incorporation of the next nucleobase unit.

The sequencing can be single-molecule template or multi-molecule template. Single-molecule sequencing means that an individual sequence is read from an individual circular template molecule. Multi-molecule sequencing means that a plurality of template molecules are sequenced together to generate a consensus sequence without resolving individual template sequences. A consensus sequence means a sequence formed from the most frequently represented nucleobase units at each position with the possible exception that a certain positions a majority nucleobase unit and at least one minority nucleobase unit are designated. In such sequencing, the plurality of templates usually contain copies of the same target nucleic acid segment, which can be identical among different templates or show variation due to variants of the target nucleic acid sequence (e.g., allelic or viral variants). Sequencing a plurality of templates simultaneously detects incorporation of a consensus nucleobase unit at successive positions of a nascent chain. If variation is present among the target nucleic acid segments in the template, majority and minority nucleobase units can sometimes be detected at the positions of such variation.

In some methods, the nucleobase units being incorporated bear fluorescent (or other detectable) labels. Preferably, each of the different nucleobase units used bears a different fluorescent (or other) label to allow differential detection of the nucleobase units. However, in some methods different nucleobase units have the same label. In such methods, the different nucleobase units can be distinguished by being supplied sequentially.

Incorporation of a nucleobase unit can be detected by measuring the presence of label on a nucleobase unit being incorporated. In some methods, the incorporation of nucleobase units is detected by measuring the release of a label from the nucleobase unit being incorporated. A preferred approach as with SMRTbell™ template sequence is to use nucleobase units fluorescently labeled on the terminal phosphate of the nucleobase unit. (Korlach et al., *Nucleosides, Nucleotides and Nucleic Acids,* 27:1072-1083, 2008. The label is cleaved from the nucleotide monomer on incorporation of the nucleotide into the polynucleotide. Accordingly, the label is not incorporated into a nascent nucleic acid, increasing the signal:background ratio. Sequencing can be performed in a single-molecule, real-time (SMRT™) format as described in U.S. Pat. Nos. 7,181,122, 7,302,146, and 7,313,308. In such a format, circular templates are sequenced individually and an incorporated nucleobase unit is detected in real time before incorporation of the next incorporated nucleobase unit. Sequencing of an individual templates can take place in a cylindrical metallic chamber known as a zero mode waive guide, and many such individual templates each in its own zero mode waive guide can be sequenced in parallel.

Another nucleobase units uses a fluorescent dye linked to photocleavable chemical moiety to cap the 3'—OH group of deoxynucleoside triphosphates (dNTPs) (Welch et al. Nucleosides and Nucleotides 18, 197 (1999) & European Journal, 5:951-960 (1999); Xu et al., U.S. Pat. No. 7,777, 013; Williams et al., U.S. Pat. No. 7,645,596; Kao et al, U.S. Pat. No. 6,399,335; Nelson et al., U.S. Pat. Nos. 7,052,839 & 7,033,762; Kumar et al., U.S. Pat. No. 7,041,812; Sood et al, US Pat. App. No. 2004-0152119; Eid et al., Science 323, 133 (2009)).

Figure 7:
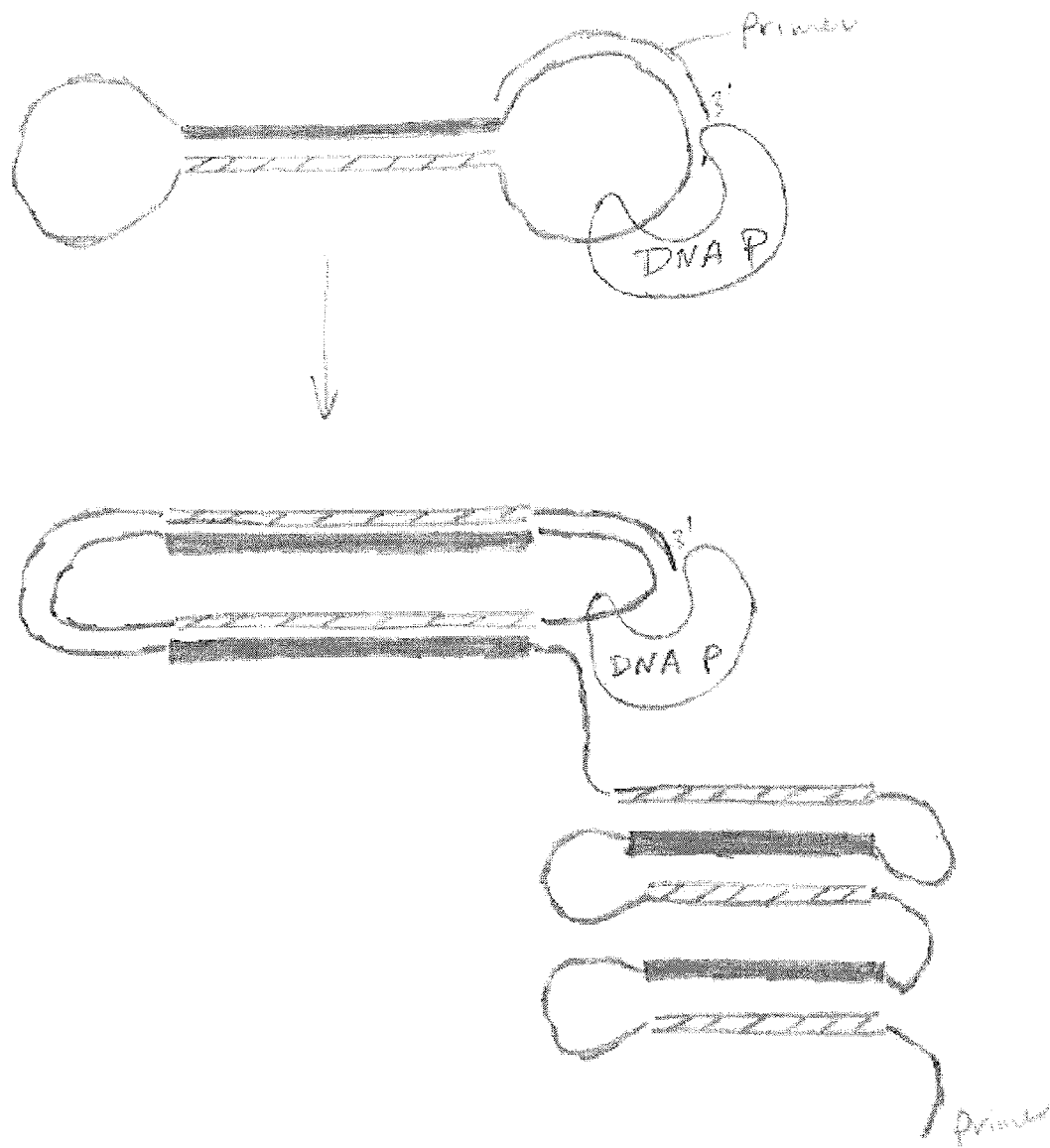
FIGS. 7A, B: Comparison of sequence reads from a SMRTbell™ template (A) and a circularized template of the present invention (B).
Figure 7:
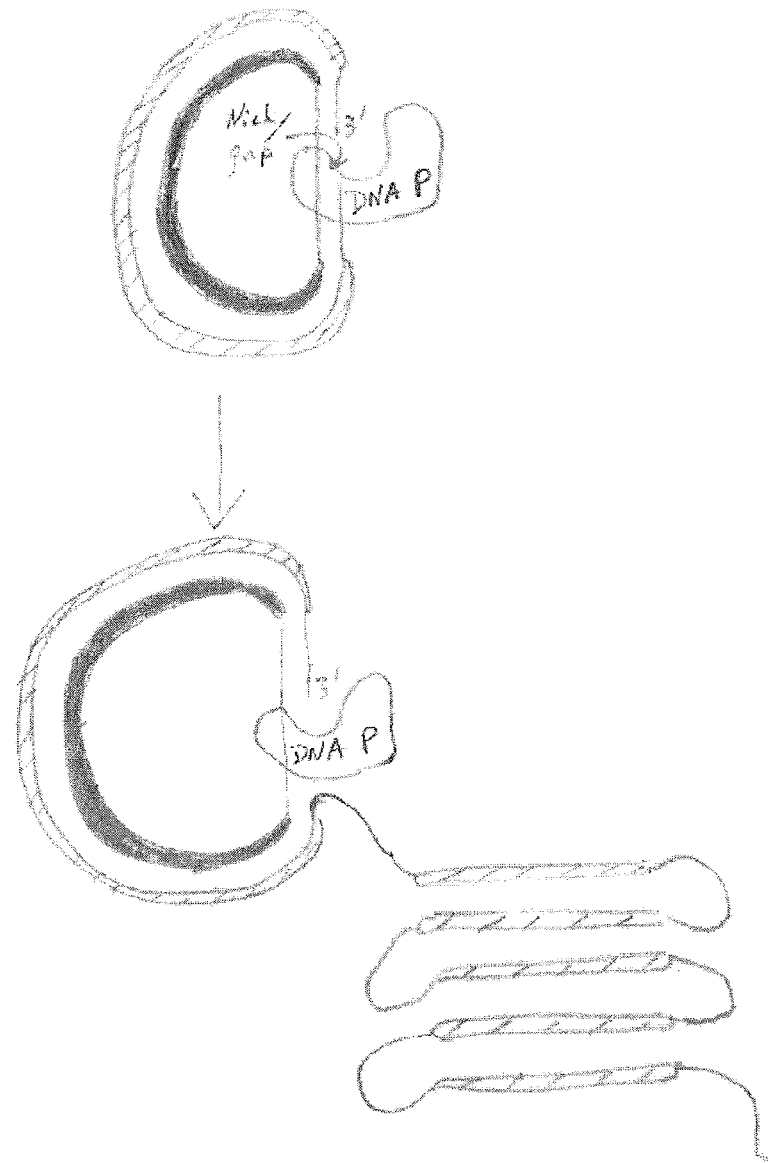

In some methods, the incorporation of nucleobase units into the nascent chain is detected by measuring a chemical change that occurs during the incorporation of nucleobase units. The chemical change can be a change in pH as for the Ion Torrent Personal Genome Machine (Guilform, Conn.), which detects hydrogen ions. The chemical change can alternatively or additionally be release of a pyrophosphate. Pyrosequencing detects the release of inorganic pyrophosphate (PPi) as particular nucleotides are incorporated into the nascent strand (Ronaghi, et al., *Analytical Biochemistry* 242(1):84-9, 1996; Ronaghi, M., *Genome Res.* 11(1):3-11, 2001; Ronaghi, et al., *Science* 281(5375):363, 1998; U.S. Pat. Nos. 6,210,891, 6,258,568 and 6,274,320). Released PPi can be detected by, e.g., a process in which the released PPi is immediately converted to adenosine triphosphate (ATP) by ATP sulfurylase, and the level of ATP generated is detected via luciferase-produced photons measuring pyrophosphate release upon testing DNA/polymerase complexes with each deoxyribonucleotide triphosphate (dNTP) separately and sequentially When sequencing proceeds around the circular template multiple times, a sequencing read is generated containing tandem reads of the target nucleic acid spaced by a segment representing the rest of the circular template, which can be a segment comprising or consisting of primer segments formed by the present methods. Because sequencing is initiated at a single site on the circular template, only one strand of the target nucleic acid is represented in the tandem reads of the target nucleic acid (see FIG. 7, lower). By contrast alternating strands of the a target nucleic acid are present when using a circular template with SMRTbell™ primers as previously reported (see FIG. 7, upper).

The multiple reads of a strand of the target nucleic acid segment may contain sequencing errors. Combination of these multiple reads to provide a consensus sequence can eliminate at least some of the sequencing errors.

The present methods are particularly advantageous for target nucleic acids in which mixed populations of nucleic acid molecules may be present. Such targets include polymorphic genes from a heterozygous individual (or from a pool of individuals whether or not heterozygous) as well as viral nucleic acids, which are often subject to mutation. PCR amplification of such target nucleic acids with its cycles of denaturation and annealing can generate heteroduplexes between variant forms of a target nucleic acid. Because only one strand of the target nucleic acid is sequenced per reaction, the present method avoids errors introduced by unwittingly combining sequences of both strands of a heteroduplex PCR product.

In some methods, multiple individual circulate template molecules are sequenced in parallel (or sequentially). The multiple individual template molecules can contain different variant forms of a target nucleic acid that exists as a population of forms (e.g., polymorphic variants or viral variants as disclosed further below). Sequencing of different template molecules containing different variant forms identifies the sequences of different variant forms.

VII. Target Nucleic Acids

A target nucleic acid refers to a nucleic acid molecule or population of related nucleic acid molecules that is or may be present within a sample. A target nucleic acid segment is part of a target nucleic acid defined by the 3' segments of primers used for its amplification The length of the target segment is determined by the capacity of amplification technology, sequencing technology (length of sequencing read) and whether some or all of target nucleic acid is of interest to sequence. The segment can range from about ten nucleotides to more than 1000 nucleotides or up to 10,000 nucleotides or even greater than 10,000 nucleotides. Segments of target nucleic acids having 25-10,000 nucleotides are common.

A target nucleic acid can exist in different forms, i.e., single-stranded, double-stranded, triple-stranded, or mixtures thereof, such as in a partially double-stranded hairpin structure or partially double-stranded duplex structure, and a target segment can present on any strand (sense or antisense) of the structure. A target nucleic acid can be RNA (e.g., viral RNA, micro RNA, mRNA, cRNA, rRNA, hnRNA or DNA (genomic DNA, extrachromasomal DNA, mitochondrial DNA, plasmid DNA or cDNA) among others. The target nucleic acid can be from a pathogenic microorganism, such as a virus, bacteria or fungus, or can be endogenous to a patient. A target nucleic acid can be synthetic or naturally occurring.

Viral nucleic acids (e.g., genomic, mRNA) form a useful target for analyses of viral sequences. Some examples of viruses that can be detected include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, comovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus.

Analysis of viral nucleic acids is particularly useful for analyzing drug resistance. Viruses mutate rapidly so that a patient is often infected with a heterogeneous population of viral nucleic acids including majority and minority forms, which changes over time. Some of the mutations differentiating species of the heterogeneous population may be associated with resistance to a drug that the patient has been treated with or may be treated with in the future. Deconvolution of the population to detect individual variants allows detection of drug resistant mutations and their change over time, thus allowing treatment regimes to be customized to take into account the drug resistance of strains infecting a particular patient. Because drug-resistant or other mutations may present as only a small proportion of viral nucleic acid molecules, sequencing of a large number of molecules in the viral nucleic population may be required to provide a high likelihood of identifying all drug resistant mutations or at least all, whose representation as a percentage of the total viral nucleic acid population exceeds a threshold.

Human nucleic acids are useful for diagnosing diseases or susceptibility towards disease (e.g., cancer gene fusions, BRACA-1 or BRAC-2, p53, CFTR, cytochromes P450), for genotyping (e.g., forensic identification, paternity testing, heterozygous carrier of a gene that acts when homozygous, HLA typing), determining drug efficacy on an individual (e.g., companion diagnostics) and other uses. The methods are particularly useful for analyzing target nucleic acids or segments thereof including site(s) of polymorphic variation between individuals, such as multiallelic genes. In heterozygotic individuals, two or more variants of a target nucleic acid are present in a single sample. The variants can pair with one another in PCR forming a heteroduplex. If both strands of a target nucleic acid are read from a circular duplex, then the different allelic sequences may be unwittingly combined into a single consensus sequence. However, in the present methods only one strand target strand is read from a given template so that variant alleles read from different templates are kept separate.

rRNA is particularly useful for detecting and/or typing pathogenic bacteria. Examples of such bacteria include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, Lymes disease bacteria, streptococci, or *neisseria*.

Small RNA can also be sequenced. For example, small RNAs (about 17-27 nt), such as microRNA (miRNA), small or short interfering RNAs (siRNA), short hairpin RNAs (shRNA), and small nuclear RNAs.

VIII. Kits

Any of the primer pairs mentioned above, optionally in combination with any of the enzymes (e.g., polymerase with 3'-5' exonuclease activity) or ligase can be packaged as a kit. Such a kit can also include instructions for performing any of the methods described above.

EXAMPLES

Example 1

This example describes a simple scheme for practice of the above methods illustrated by FIGS. 1-4. The upper portion of FIG. 1 shows first and second primers with three segments. The 3' segment is a standard target binding region just like normal PCR primers. The middle segment is a short "TT cushion." The 3' segment is a "GC region" that is complementary in the forward and reverse primers for a single target to be circularized. Only one of the primers has a 5' phosphate to serve as ligation substrate.

The primers are contacted with a target nucleic acid polymerase and nucleobase units under conditions suitable for PCR. A few cycles of PCR generates the amplification product shown at the bottom of FIG. 1 with the target nucleic acid segment flanked by the primers duplexed with their complementary sequences. The amplification product can then be purified to separate it from nucleobase units and the polymerase.

The amplification product is then treated simultaneously (or separately) with T4 DNA polymerase and T4 DNA ligase in the presence of only dATP for this primer design as shown in FIG. 2. The ligation reaction using T4 DNA ligase includes ATP.

The T4 polymerase 3'-5' exonuclease activity removes G and C nucleotides until it reaches the "AA" complement of the "TT cushion," where it can then use the dATP to fill back in, effectively stopping the removal of nucleotides (FIG. 2 right).

The single-stranded complementary 5' segment of the primers are now revealed, so they can anneal to each other at the temperature of the T4 DNA ligase reactions take place (FIG. 2 middle and lower). The complementary ends preferably do not anneal at the higher temperatures at which PCR is performed.

When annealed, the 5' end with a phosphate is adjacent a newly revealed 3'OH of the "AA" complement of the cushion" forming a substrate that is ligated with T4 DNA ligase (FIG. 3). The other 5' end does not have a phosphate and therefore cannot be ligated. This leaves a "nick", in which the free 3'OH is extended by the sequencing polymerase to initiate the sequencing reaction (FIG. 3).

Example 2

Figure 4:
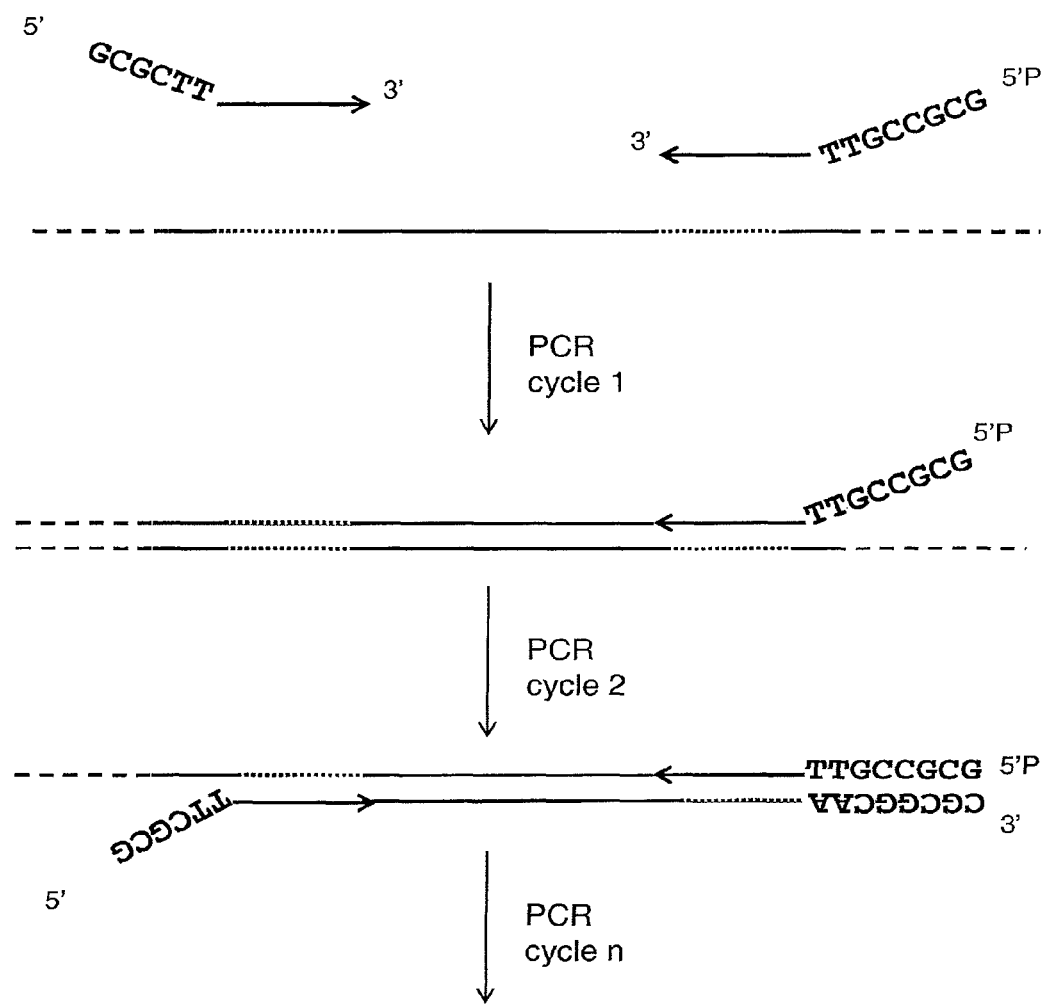
FIGS. 4-6 shows a scheme for generating a circularized template with a gap adjacent to a free 3' hydroxyl group.
Figure 5:
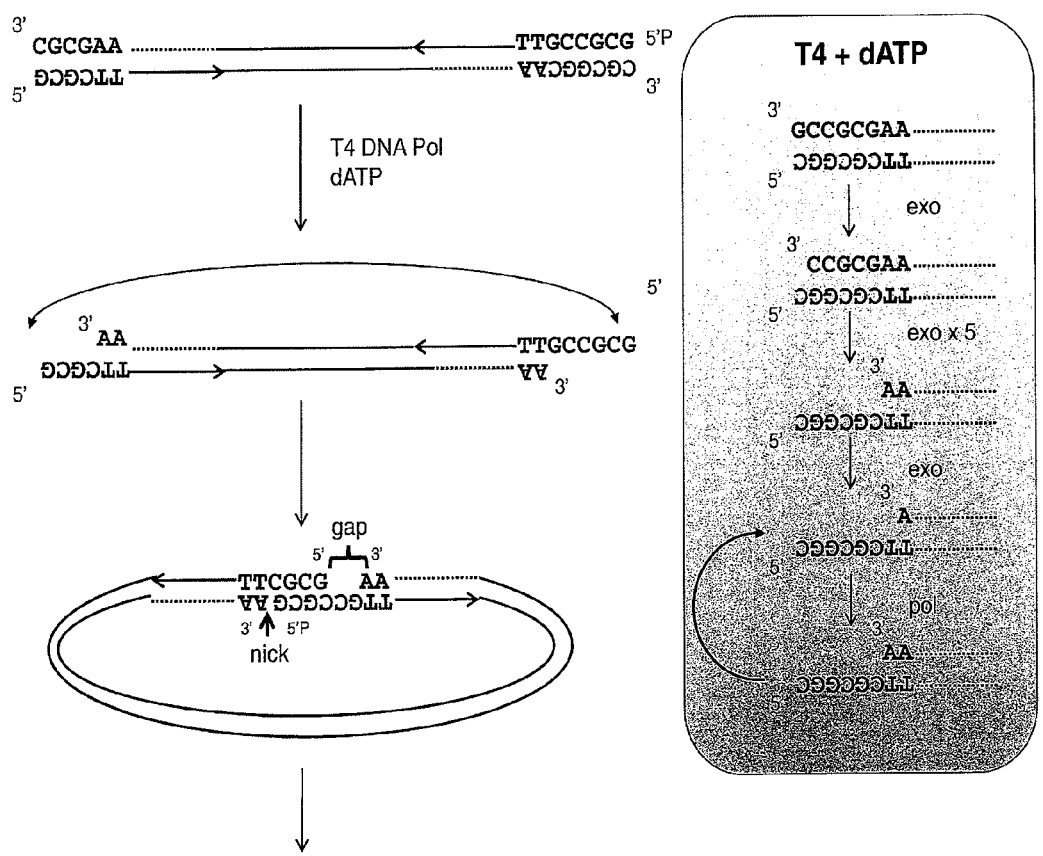
Figure 6:
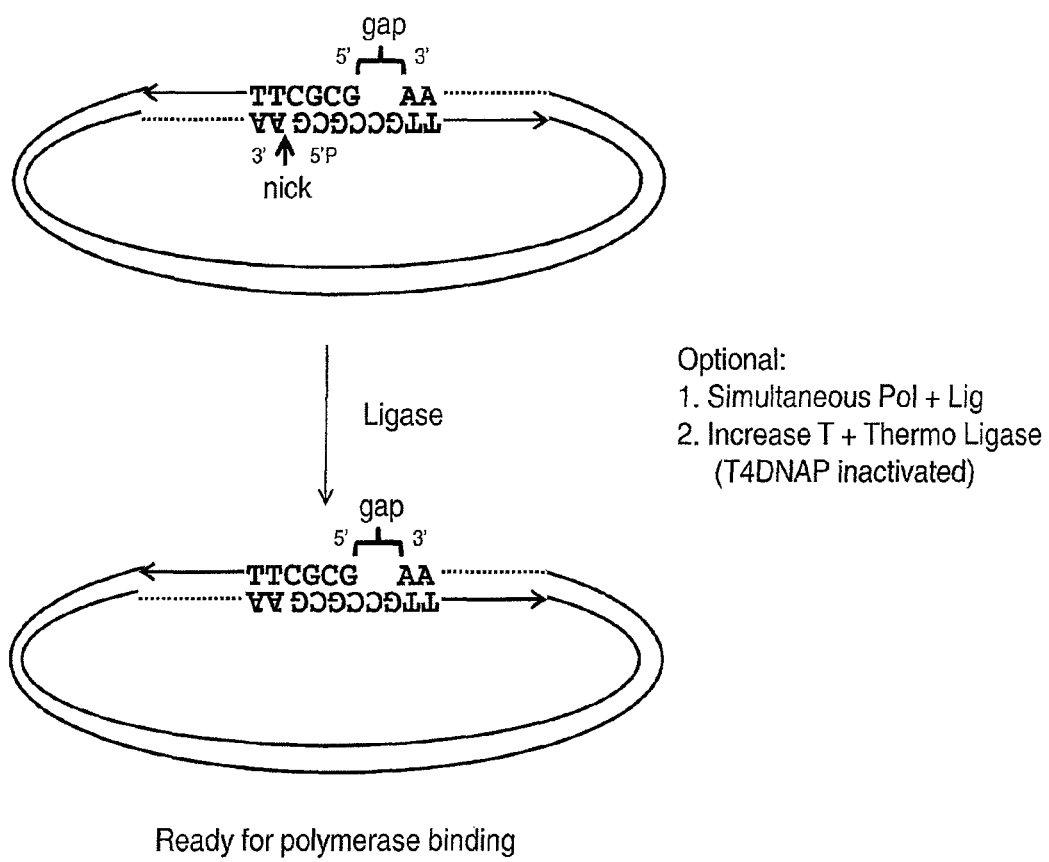

Example 1 produces a simple nick for the sequencing polymerase to bind to and extend from. Example 2 describes a variation to generate a gap instead of a nick, as shown in FIGS. 4-6. First, primers are designed with GC 5' segments and a "TT cushion" segment region (of course, these could be reversed). However, the GC segments are of unequal length, the shorter segment being on the unphosphorylated primer (see FIG. 4). PCR is performed as in Example 1.

PCR produces the amplicon shown in FIG. 4 lower and FIG. 5 upper. The "GC region" is on the ends, with the "TT cushion" duplexed with its AA complement just inside it.

The amplicon is digested with T4 DNA polymerase with only dATP present in solution. The exonuclease activity of the T4 polymerase removes the complements of the 5' GC segment. However, when the complement of the "TT cushion" is reached, the T4 polymerase can just add in an A after it remove one, so the cushion remains intact (FIG. 5, right). The molecule then circularizes via annealing of single-stranded 5' ends (FIG. 5, lower, FIG. 6, upper). The nick between the 5' phosphate and adjacent 3' hydroxyl is sealed by ligase (FIG. 6 upper). The gap between the other 5' primer end and adjacent 3' hydroxyl of an AA complement of a TT cushion remains (FIG. 6, lower). The 3' hydroxyl provides a site for template-directed extension in a polymerase reaction.

Example 3:

Generation of a Nicked Circularized Template for Sequencing from an HLA-A Target Nucleic Acid This example describes the preparation of a circularized template for sequencing from a target nucleic acid that was a gene coding for human leukocyte antigen A (HLA-A). HLA-A target nucleic acid was isolated genomic DNA obtained from an HLA Reference Panel (University of California, Los Angeles Immunogenetics Center, part # C1-223).

The primers used in this example each include a 5' segment, and a cushion segment that do not hybridize with the target nucleic acid. The primers in this example each also include a 3' segment that hybridizes with the target nucleic acids. Thus, the pair of primers used in this example are configured as follows: (SEQ ID NO:1 first primer), 5'-GCCCGCGG<u>AAAAAA</u>CAAGTCACAAAGGGAAGG GCAGGAAC-3', wherein underlined residues 1-8 are the 5' region, double underlined residues 9-14 are the cushion segment, and residues 15-40 are the 3' segment; and (SEQ ID NO:2 second primer) 5'-<u>CCGCGGGC AAAAAA</u>GGATACTCACGACGCGGACCCAG-3', wherein underlined residues 1-8 are the 5' segment, double underlined residues 9-14 are the cushion segment, and residues 15-37 are the 3' segment. In this example, the 5' residue of the first primer had a 5'-phosphate, and the 5' residue of the second primer did not have a 5'-phosphate.

A PCR reaction was performed on the HLA-A target nucleic acid using the first and second primers (SEQ ID NOS: 1 and 2). Briefly, 100 nanograms of purified target nucleic acid was added to each of 12 wells of a 96 well plate. Each of the 12 wells of the plate contained 50 microliters of a PCR reaction mix. The PCR reaction mix was made according to manufacturer's instructions to contain Herculase II Fusion DNA polymerase (Agilent Technologies, part #600675) in the Herculase II Reaction Buffer and further contains 250 µM of each dNTP and 0.25 microM of each primer. An amplification reaction was then performed under the following cycling parameters: 2 minutes at 95° C. for initial denaturation and enzyme activation, followed by 35 cycles of 20 sec denaturation at 95° C., 20 sec annealing at 69° C., and 1 min 40 sec extension at 72° C. Amplicons were about 3 kb in length. Amplicons were purified using QIAquick PCR Purification Kit (Qiagen, part #28106). From 2 to 4 microgram of purified amplicon was obtained from each of 50 microliter amplification reactions.

Amplification products from the amplification reaction were then transferred to a reaction for generating the circular template. For the circularization reaction, 1 microgram of each amplification product was combined with 6U T4 DNA Polymerase, 800U T4 DNA Ligase, T4 DNA Ligase Buffer (New England Biolabs, part # MO203, #MO202 and # B0202), 60 microM dTTP (Life Technologies, part #55085) and water to 100 microliters. The reactions were then incubated for 30 minutes at room temperature, followed by an enzyme inactivation step for 10 minutes at 70° C. Circularized templates having a nick between the 5' end of the second primer and the 3'-OH of the adjacent nucleobase are then selected for by digesting fully double stranded linear templates using 15U Lambda Exonuclease (New England Biolabs, part # MO262) and digesting single stranded nucleic acids using 5U Exonuclease VII (USB Affymetrix, part #70082Z). The selection reactions were incubated at 37° C. for 30 minutes, and then nicked circularized templates were purified using MinElute columns (Qiagen, part #28006). Purified templates were quantitated using a Qubit fluorometer and Qubit dsDNA HS Assay Kit (Life Technologies, part # Q32851). They were further visualized on a 1.2% E-gel (Life technologies, part # G5018-01). Bands seen at 5 kb on the 1.2% E-gel, relative to a NEB 2-Log DNA Ladder (NEB, part # N0469) represented the nicked 3 kb circularized template.

Circularized and nicked template was then prepared for a sequencing reaction on a Pacific Biosciences RS sequencer. Briefly, circularized and nicked template was bound to the polymerase provided with the DNA Polymerase Binding Reagent Kit 8 (Pacific Biosciences, part #001-359-802), and binding procedure was performed according to manufacturer instructions, with the exception that the sequencing primer and the sequencing primer annealing step was omitted from the procedure. Circularized and nicked template with bound polymerase was then loaded into SMRT™ cells and a sequencing reaction was performed on an RS sequencing instrument (Pacific Biosciences).

Example 4:

Generation of a Gapped Circularized Template for Sequencing from an HLA-A Target Nucleic Acid The procedure was exactly the same, except that a new 5'-phosphorylated primer was used instead of the "first primer" in Example 3:
5'-GCCCGCGGCGGCAAAAAAACAAGTCACA AAGGGAAGGGCAGGAAC-3'. (SEQ ID NO:3), wherein underlined residues 1-12 are the 5' segment, double underlined residues 13-18 are the cushion segment, and residues 19-44 are the 3' segment.

The second primer was the same as in Example 3 (SEQ ID NO:2), and lacked a 5'-phosphate.

The circularized templates had a 4 nucleotide gap between the 5' end of the second primer and the 3'-OH of the adjacent nucleobase unit.

The examples and embodiments described herein are for illustrative purposes only. Various modifications or changes thereof are apparent and are included within the spirit and purview of this application and scope of the appended claims. All publications, patents, patent applications, web sites, accession numbers and the like cited herein are hereby incorporated by reference in their entirety for all purposes. If different versions of any such citation are available, the most recent version at the filing date of the present application is meant. Unless otherwise apparent from the context, any embodiment, aspect, step, feature, element or the like can be used in combination with any other.

What is claimed is:

1. A method of forming a circular template for sequencing a target nucleic acid, comprising:
   (a) contacting a target nucleic acid with a primer pair under PCR conditions, each of the primers having a 3' segment and a 5' segment, the 3' segments of the primers being target-binding segments, the 5' segments being mutually complementary in opposing orientations, a first of the primers having a 5' phosphate group and the second of the primers lacking a 5' phosphate and/or having a shorter 5' segment than the first primer; thereby forming an amplified nucleic acid comprising a segment of the target nucleic acid flanked by the primers duplexed with their complementary segments;
   (b) contacting the amplified nucleic acid with a nucleic acid polymerase having a 3' to 5' exonuclease activity and one or more nucleobase units in solution, wherein the polymerase with exonuclease activity digests at least parts of the amplified nucleic acid complementary to the 5' segments of the primers, the digested nucleobase units of the parts complementary to the 5' segments being of a type different than the one or more nucleobase units in solution, and the amplified nucleic acid circularizes via annealing of the 5' segments; and
   (c) contacting the circularized nucleic acid with a ligase which seals a nick between the 5' phosphate group of the first primer and an adjacent 3' hydroxyl group in a strand of the circularized nucleic acid leaving the circularized nucleic acid with a single nick or gap between the 5' segment of the second primer and a 3' hydroxyl of an adjacent nucleotide in a complementary strand thereby forming the circular template for sequencing the target nucleic acid.

2. A method of forming a circular template for sequencing a target nucleic acid, comprising:
   (a) contacting a target nucleic acid with a primer pair under PCR conditions, each of the primers having a 3' segment and a 5' segment, the 3' segments of the primers being target-binding segments, the 5' segments being mutually complementary in opposing orientations, a first of the primers having a 5' phosphate group and the second of the primers lacking a 5' phosphate and/or having a shorter 5' segment than the first primer; thereby forming an amplified nucleic acid comprising a segment of the target nucleic acid flanked by the primers duplexed with their complementary segments;
   (b) contacting the amplified nucleic acid with a nucleic acid polymerase having a 3' to 5' exonuclease activity and one or more nucleobase units in solution, the nucleobase units in solution being of a type different than the nucleobase units complementary to the nucleobase units in the 5' segments of the primers, wherein the polymerase with exonuclease activity digests at least parts of the amplified nucleic acid complementary to the 5' segments of the primers, and the amplified nucleic acid circularizes via annealing of the 5' segments; and
   (c) contacting the circularized nucleic acid with a ligase which seals a nick between the 5' phosphate group of the first primer and an adjacent 3' hydroxyl group in a strand of the circularized nucleic acid leaving the circularized nucleic acid with a single nick or gap between the 5' segment of the second primer and a 3' hydroxyl of an adjacent nucleotide in a complementary strand thereby forming the circular template for sequencing the target nucleic acid.

3. The method of claim 1, wherein each primer further comprises a cushion segment between the 5' segment and the 3' segment, the cushion segment including at least one nucleobase unit complementary to a type of the one or more nucleobase units in solution, whereby the exonuclease digestion terminates at or in the complements of the cushion segments in the amplified nucleic acid.

4. The method of claim 3, wherein the cushion segment nucleobase unit(s) consist of a single type of canonical nucleobase unit, and the 5' segment nucleobase units consist of the two canonical nucleobase types other than the single type of canonical nucleobase and its complement except that if one 5' segment is longer than the other, the extra portion of the longer 5' segment may contain the single type of canonical nucleobase unit.

5. The method of claim 3, wherein the cushion segment nucleobase units consist of two types of canonical nucleobase units complementary to one another and the 5' segments nucleobase units consist of the other two types of canonical nucleobase unit.

6. The method of claim 3, wherein nucleobase units of the cushion region consist of A, or T/U, or A and T/U, and the nucleobase units of the 5' regions consist of C and G.

7. The method of claim 3, wherein the nucleobase units of the cushion region consist of C or G, or C and G, and the nucleobase units of the 5' regions consist of A and T/U.

8. The method of claim 3, wherein a 5' segment or cushion segment of the first and/or second primer includes one or more noncanonical nucleobase units.

9. The method of claim 3, wherein all nucleobase units in the primer are canonical nucleobase units.

10. The method of claim 1, wherein the target nucleic acid is a genomic DNA molecule, or a cDNA molecule or an RNA molecule.

11. The method of claim 1, wherein the nucleic acid polymerase is a T4 DNA polymerase.

12. The method of claim 1, wherein the ligase is a T4 DNA ligase.

13. The method of claim 1, wherein the ligase is a thermophilic DNA ligase and step (c) is performed at a temperature over 40 degrees.

14. The method of claim 1, wherein the 5' segment of the first primer is longer than the 5' segment of the second primer resulting in a gap between the 5' end of the second primer and a 3' hydroxyl of an adjacent nucleotide in the amplified nucleic acid.

15. The method of claim 14, wherein the 5' segment of the first primer is longer than the 5' segment of the second primer by four nucleobase units and the gap is four nucleobase units.

16. The method of claim 1, wherein contacting steps (b) and (c) are performed at the same time.

17. The method of claim 1, wherein the PCR conditions including at least ten thermocycles.

18. The method of claim 1, wherein each of the primers has a 5' segment of at least 5 nucleobase units.

19. The method of claim 1, wherein each of the primers has a 3' segment of at least 10 nucleobase units.

20. A method for sequencing a target nucleic acid comprising the steps of:
   (a) contacting a double-stranded circularized template with a polymerase and nucleobase units, wherein the template comprises a target nucleic acid segment and a single nick or gap in one of its strands made by the method of claim 1; and
   (b) conducting template directed-extension from a free 3'-hydroxyl of a nucleobase unit abutting the nick or gap directed by the circular template incorporating the nucleobase units into a nascent chain including multiple copies of the same strand of the target nucleic acid segment; and detecting the incorporation of nucleobase units in the nascent chain to determine the sequence of the strand of the target nucleic acid segment.

* * * * *